United States Patent [19]

Sterrett et al.

[11] Patent Number: 5,074,784
[45] Date of Patent: Dec. 24, 1991

[54] ORTHODONTIC ASSEMBLY

[75] Inventors: Terry L. Sterrett, Long Beach; Haruyasu Yawata, Huntington Beach; Lawrence P. Phaneuf, Fontana, all of Calif.

[73] Assignee: Ormco Corporation, Glendora, Calif.

[21] Appl. No.: 426,043

[22] Filed: Oct. 24, 1989

[51] Int. Cl.⁵ .............................................. A61C 3/00
[52] U.S. Cl. ........................................ 433/18; 433/19; 433/21
[58] Field of Search ........................... 433/18, 19, 21, 5

[56] References Cited

U.S. PATENT DOCUMENTS

| | | | |
|---|---|---|---|
| 3,618,214 | 11/1971 | Armstrong | 433/19 |
| 3,654,702 | 4/1972 | Kelly | 433/19 |
| 3,690,003 | 9/1972 | Gerbey | 433/8 |
| 3,772,789 | 11/1973 | Weoskin | 433/5 |
| 3,798,773 | 3/1974 | Northcutt | 433/19 |
| 3,921,295 | 8/1974 | James | 433/21 |
| 3,936,938 | 2/1976 | Northcutt | 433/21 |
| 3,997,970 | 12/1976 | Hodgson | 433/19 |
| 4,037,324 | 7/1977 | Andreasen | 433/21 |
| 4,199,865 | 4/1980 | Cain | 433/21 |
| 4,225,139 | 3/1981 | Ladanyi | 433/21 |
| 4,315,739 | 2/1982 | Cain | 433/21 |
| 4,382,783 | 5/1983 | Rosenberg | 433/19 |
| 4,462,800 | 7/1984 | Jones | 433/19 |
| 4,472,139 | 9/1984 | Rosenberg | 433/19 |
| 4,600,382 | 7/1986 | Forster | 433/5 |
| 4,708,646 | 11/1987 | Jasper | 433/19 |
| 4,795,342 | 1/1989 | Jones | 433/19 |
| 4,849,032 | 7/1989 | Kawaguchi | 148/11.5 R |
| 4,872,836 | 10/1989 | Grove | 433/5 |
| 4,875,856 | 10/1989 | Grussmark | 433/18 |

FOREIGN PATENT DOCUMENTS 3402943  8/1985  Fed. Rep. of Germany ........ 433/21

Primary Examiner—Robert P. Swiatek
Assistant Examiner—Nicholas D. Lucchesi
Attorney, Agent, or Firm—Marjama & Pincelli

[57] ABSTRACT

An orthodontic tensioning device and method of assembly. The device comprises at least one elastic tensioning member and a second tensioning member made of a non-elastic material provided for cooperation with the elastic tensioning member so as to provide a predetermined tensioning member.

10 Claims, 7 Drawing Sheets

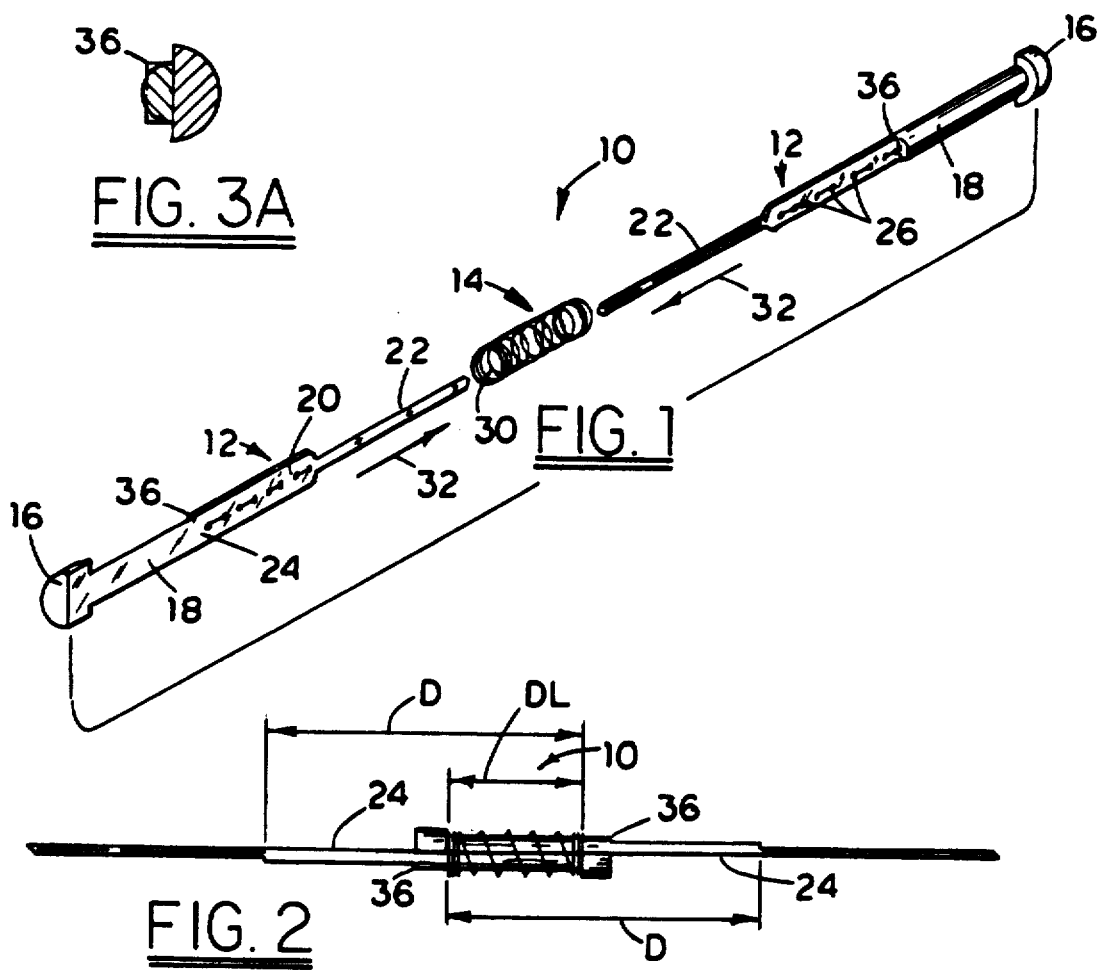
FIG. 3A
FIG. 1
FIG. 2
FIG. 3
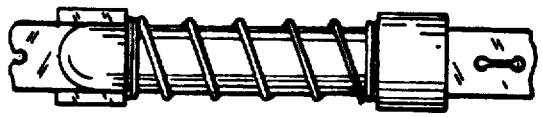
FIG. 4
FIG. 5

ORTHODONTIC ASSEMBLY

The present invention relates to an orthodontic tensioning device. More particularly, to an orthodontic tensioning device having one end attached to the upper or lower jaw and the other end connected to a point on the same jaw or other jaw in order to correct malocclusions of teeth and/or jaws.

BACKGROUND OF THE INVENTION

In the practice of orthodontia it is often necessary to move into a more favorable position at least one tooth with respect to the other teeth. This is accomplished typically through the use of what is referred to as Class II-Type Devices which usually comprise the provision of an elastic member or coil spring between one point on a tooth or archwire on one of the jaws to a tooth or point on the archwire on the other jaw. Examples of orthodontic tensioning devices of the prior art are illustrated in U.S. Pat. Nos. 3,618,214; 3,654,702; 936,938; 3,921,295; 4,199,865; 4,315,739; 4,382,783; 4,462,800; 4,849,032; and 4,330,271. As can be seen from the foregoing patents, prior art tensioning devices come in a variety of forms.

While prior art elastic tensioning devices such as rubberbands and the like provide a wide degree of motion, a significant problem with such devices is that reliance is often placed on patient cooperation as these devices are required to be changed quite frequently. An additional disadvantage of elastic-type devices is that after a short time, these devices exhibit stress relaxation which results in substantially less force than that needed to maintain the elastomer in its stretched position, thus reducing the amount of force being applied. A still further problem with such devices is that they take a permanent set reducing its effectiveness at lower elongations.

Steel coil springs and other mechanical-type devices which exist in the prior art have the disadvantage in that the amount a patient may open his mouth is limited, or becomes extremely uncomfortable the wider the patient opens his mouth. Furthermore, with typical prior art steel coil springs, the force applied varies widely in response to large deflections which result in a wide variation of forces being applied to the tooth as the patient opens and closes his or her mouth. Another problem with prior art-type devices is that occasionally a patient may open his mouth to such an extent that the tensioning device will go beyond its elastic limit. The tensioning device is so stretched and a permanent set takes place, thus reducing the effectiveness of the device, especially when the patient has his mouth closed or barely open. Further, open coil springs present the possibility of trapping food therein.

Applicants have invented an improved orthodontic tensioning device which minimizes or avoids the problems the prior art. The orthodontic tensioning device of the present invention provides a relatively constant force to the malocclused teeth or jaws, is capable of high elongation and maintaining a substantial portion of the initial force applied. Further, the device is simple to assemble, of relatively low cost to manufacture, easy to use, and provides means for easily adjusting the force to be applied.

SUMMARY OF THE INVENTION

In one aspect of the present invention, there is provided an orthodontic tensioning device having at least one elastic tensioning member Means are provided for cooperating with the elastic tensioning member for compensating, at least in part, for any relaxation that may occur in the elastic member In another aspect of the present invention there is provided a pair of elastic tensioning members made of an elastic material. A coil spring is placed around both elastic members and is designed to cooperate with the elastic member so as to provide a predetermined tensioning force.

In yet another aspect of the present invention, there is provided a method of assembling an orthodontic tensioning device comprising:

a) providing a pair of elongated members, each of the elongated members having an outer terminal end, a central body section, a retention section, and an inner detachable tail section;

b) providing a coil spring member having an inner opening of sufficient size to allow placement of the pair of elastic members therethrough; and c) passing through the inner detachable tail section of each of the elastic members through opposite ends of the spring and pulling through the detachable tail section through the other end so as to cause the terminal end of the elastic tensioning members to rest against the closest end of the spring.

DESCRIPTION OF THE DRAWINGS

FIG. 1 is an exploded perspective view of a orthodontic tensioning device made in accordance with the present invention;

FIG. 2 is a top plan view of the device of FIG. 1 in the assembled state;

FIG. 3 is a front elevational view of the device of FIG. 2;

FIG. 3a is a cross-sectional view of the device of FIG. 3 taken along line 3a.

FIG. 4 is an enlarged fragmentary view of a portion of the device illustrated in FIG. 3 as illustrated by line 4—4;

FIG. 5 is a view similar to FIG. 4 illustrating the device when tension is being applied;

DETAILED DESCRIPTION OF THE PREFERRED EMBODIMENTS

Figure 6:
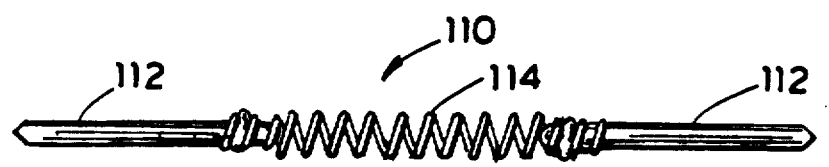
FIG. 6 is a top plan view of another embodiment of an orthodontic tensioning device made in accordance with the present invention.

Referring to FIGS. 1-4, there is illustrated an orthodontic tensioning device/assembly 10 made in accordance with the present invention. The assembly 10 includes a pair of elongated elastic tensioning members 12 and a coil spring 14. Each of the elongated elastic tensioning members 12 comprise an outer terminal end 16, a central body section 18, a retention section 20 adjacent central body section 18, and a inner detachable tail section 22 at the end of retention section 20 The elastic tensioning members 12 are each integrally formed, preferably by molding, and include a common mating surface 24 along which the pair of elongated members 12 slide. In the assembled state, the coil spring 14 is positioned adjacent the central body section 18, and holds the pair of elastic tensioning members 12 so that mating surfaces 24 slide relative to one another in response to an axial force placed on the retention section 20. The retention section 20 is provided with means for attachment to an orthodontic fixture within the mouth of a patient. In the particular embodiment illustrated, there is provided a plurality of substantially dumbbell-shaped openings 26 in retention section 20 that are designed to engage a hook 28 or other orthodontic fixture, for example, but not limited to, an orthodontic bracket.

The orthodontic tensioning assembly 10 is easily assembled by simply passing the detachable tail section 22 of each tensioning member 12 through the central opening 30 of coil spring 14 starting at opposite ends thereof The detachable tail sections 22 each have a shape and length such that they can easily pass through central opening 30 simultaneously, and grasped as it exits central opening 30. Once the detachable tail sections 22 have passed through central opening 30, they are each clasped and pulled in opposite axial directions as indicated by arrows 32 so that mating surfaces 24 of members 12 are adjacent one another. Since the members 12 are made of an elastic material, they stretch and elongate and thus enable their passage through central opening 30 of coil spring 14 quite easily. For the purposes of this invention, an elastic material shall be considered a material that can elongate substantially without any substantial permanent deformation, for example elongations greater than about 50%. Examples of such materials are rubbers and elastomers presently available. In the embodiment illustrated, members 12 are both made of an elastic polyurethane. The members 12 are pulled through until the spring 14 mates with the terminal ends 16 which is integrally formed with member 12. In the particular embodiment illustrated, each terminal end 16 has a configuration which is substantially that of a semicircle, and has a diameter at least equal to or greater than the outside diameter of the coil spring 14 so as to prevent the coil from any further axial movement along the member 12. Once the orthodontic tensioning assembly 10 has been assembled, as illustrated in FIGS. 2 and 3, detachable tail sections 22 may be removed, for example, by simply cutting tail section 22 from retention section 20. However, if desired, detachable tail sections 22 may be removed after placement on the orthodontic fixtures as the detachable section may be of further use in mounting the retention sections 20 onto the appropriate orthodontic fixture. Once assembled, the central body section 18 of the pair of elastic tensioning members 12 substantially fills the central opening 30 of coil spring 14. The orthodontic tensioning device 10 is provided with means to prevent the assembly from simply coming apart in the unrelaxed state to make assembly easier and maintain the spring in the appropriate assembled position. In the particular embodiment illustrated, this is accomplished by providing retention section 20 with a pair of stop sections 36 which mate with the outer end of coil spring 14. This can be seen in FIG. 3(a). While in the assembled state, stop sections 36 extend adjacent the outer end of the coil springs, during assembly of the device 10, the tensioning members 12 are elongated, thus causing the wider stop sections 36 to deform and flex inwardly so as to allow passage passing through the central opening 30 of coil spring 14 during initial assembly. However, once assembled, the spring 14 will be maintained in position during the relaxed position, when the spring 14 is in the tension state, the terminal ends 36 will maintain the spring 14 in its appropriate position.

Figure 12:
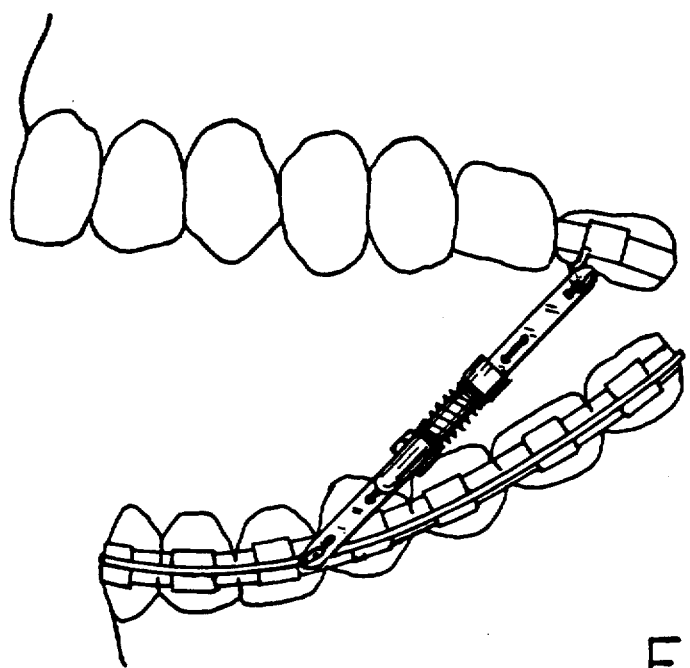
FIG. 12 is a side elevational view of the teeth of a patient's mouth having a device of FIGS. 1-5 mounted thereon when the mouth is in the open state.
Figure 13:
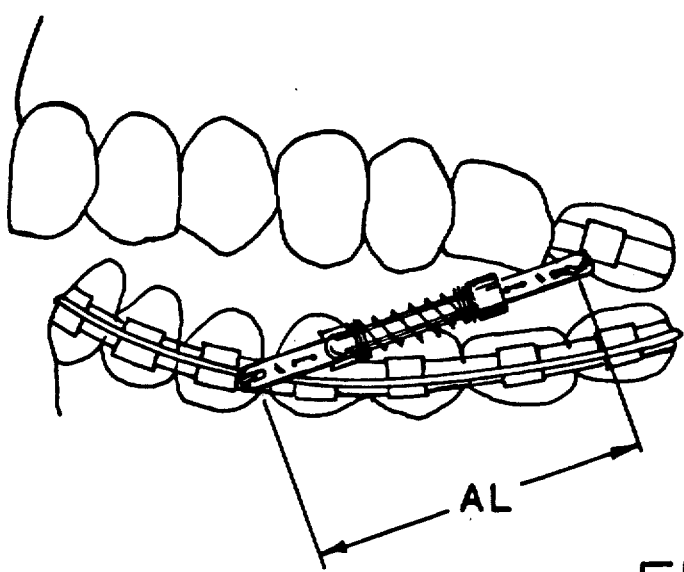
FIG. 13 is a view similar to FIG. 12 illustrating the mouth in the relatively closed position.

Referring to FIGS. 12 and 13, there is illustrated the device 10 of FIGS. 1-5 as mounted to the teeth of a patient. As can be seen, one retention section 20 is secured to a hook on an orthodontic bracket secured to a rear molar of the upper jaw and the retention section 20 of the other tensioning member 12 is secured to a hook secured to an orthodontic bracket bonded to a tooth on the lower jaw. FIG. 12 illustrates the patient wherein the upper and lower jaws are relatively wide open. FIG. 13 shows the patient with his jaws in the relatively closed position. It can be seen as the patient opens his mouth to the wider extended position as illustrated in FIG. 12, the tensioning device 10 will extend to compensate for the additional difference that is stretched. In this regard, the elastic tensioning members 12 elongate, and coil spring 14 is thus caused to compress as illustrated in FIG. 5. As time proceeds, a certain amount of relaxation may occur, or permanent set may occur in elastic member 12. In response to this, the coil spring 14 will place additional force on elastic members 12 at the terminal ends 16 so as to cause each member 12 to slide in opposite directions. This results in further displacement of member 12 and compensates, for at least some amount, for the reduction in force resulting from relaxation. Preferably, the coil spring 14 is made of a shape memory alloy, for example Nitinol. Nitinol shape memory alloys are known, for example, as described in U.S. Pat. No. 4,037,324, which is hereby incorporated by reference. Such alloys are known to have unusual properties in that they are quite ductile when below a critical temperature (known in the literature as transition temperature range or TTR) due to martensitic shear wherein adjacent places of atoms shift by a distance less than a full interatomic distance. When a body deformed in this manner is heated above its critical temperature (TTR), it displays the characteristic of mechanical memory, returning toward its original or pre-deformation shape. It is believed that strong, energetic and directional electron bonds operate to pull the displaced atoms back to their previous positions. However, it is to be understood that the coil spring 14 may be made of any conventional-type spring material so desired, for example, spring steel. It is preferred that spring 14 be made of a shape memory alloy, as this type spring provides a substantially constant force over a relatively broad deflection range. This enhances the ability of the orthodontic tensioning assembly 10 to provide a substantially constant force. Additionally, the shape and material selection of the elastic tensioning members 12 are selected such that the material is preferably elongated within the range wherein a relatively constant force is produced by the members 12. The spring 14 and members 12 are selected so as to prove a substantially constant force in the range of about 2 to 10 ounces, preferably for about 4 to 8 ounces. Preferably, elastic members 12 are made of a material having modules of elasticity in the range of about 300 to 1300 psi at 100 percent elongation. While in the preferred embodiment, members 12 are both made of the same elastic material, if desired, different elastic material having different elastic properties, may be used or only one member may be made of an elastic material, or neither member 12 may be made of an elastic member and the spring 14 provided would provide the entire elastomeric aspect of the device.

Figure 7:
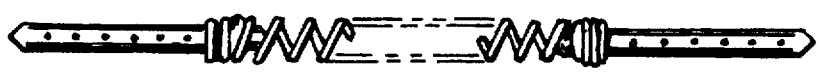
FIG. 7 is front elevational view of the device of FIG. 6.
Figure 8:
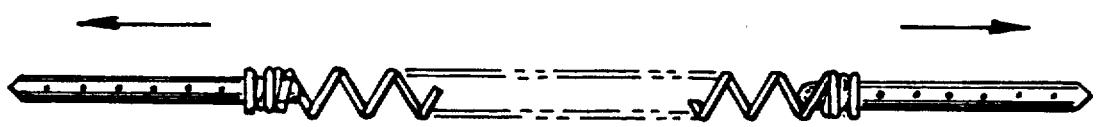
FIG. 8 is a front elevational view of FIG. 7 illustrating the device in the elongated state.

Referring to FIGS. 6-8, there is illustrated a modified embodiment made in accordance with the present invention. In the embodiment illustrated in FIG. 6, there is provided an orthodontic tensioning device 110 comprising a pair of elongated elastic tensioning members 112 which are connected in series with a coil spring 114. In this particular embodiment, the coil spring 114 is placed in tension during use, as opposed to compression of spring 14 in the embodiment of FIGS. 1-5. FIG. 8 illustrates the device 110 in the elongated position. As can be seen, the elastic members 112 stretch as does the coil spring 114. As the elastic members 112 relax, the spring will compensate for tension lost, by maintaining at least part of the force that is originally applied to the bracket. In the embodiment of FIGS. 6-8, the coil spring 114 is preferably made of a shape memory alloy as discussed with regard to FIGS. 1-5, however, the spring 114 may be made of a common spring steel if so desired.

Figure 9:
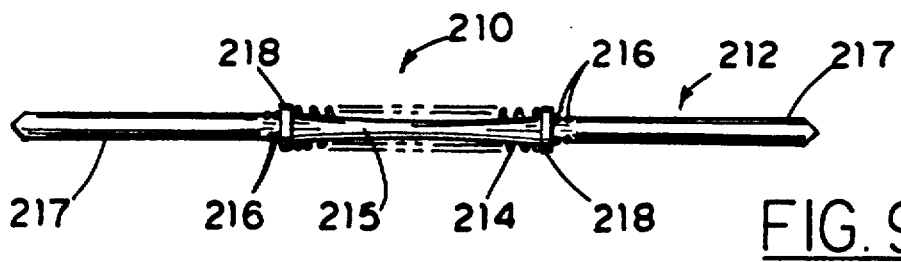
FIG. 9 is a top plan view of yet another embodiment of a device made in accordance with the present invention.
Figure 10:
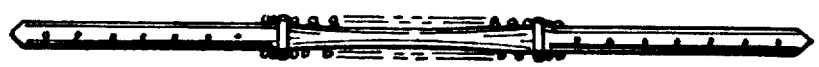
FIG. 10 is a front elevational view of the device of FIG. 9.
Figure 11:
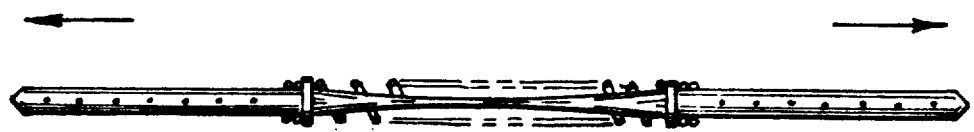
FIG. 11 is a front elevational view similar to FIG. 10 illustrating a device in the elongated state.

Referring to FIGS. 9-11, there is illustrated yet another embodiment of a device 210 made in accordance with the present invention. In this particular embodiment, device 210 comprises a single elastic tensioning member 212 having a central section 215 and a pair of outer sections 217. A coil spring 214 is secured at two axially spaced points 216 on member 212. Preferably, as illustrated, the central portion 215 of the elongated member 212 between the ends of the coil 214 has a reduced cross-sectional area, for example, a substantial hour glass shape. The outer ends of the spring 214 are secured to elongated member 212 by a pair of projections 218, and in the particular embodiment illustrated, the ends of the coil spring 214 are simply crimped on to projection 218. However, the ends of coil spring 214 may be secured in any desired manner. As the orthodontic tensioning device 212 is elongated as illustrated in FIG. 11, the outer section 217 of the elastic tensioning members 212 elongate, as does the central portion 215. Thus, the spring 214 and the central portion 215 act in parallel, and the outer sections 217 and the coil spring 214 act in series. As the outer sections 213 of the elastic member 212 relax, the inner springs will continue to provide additional axial support to assist in maintaining the initial force placed on the device 210.

Figure 14:
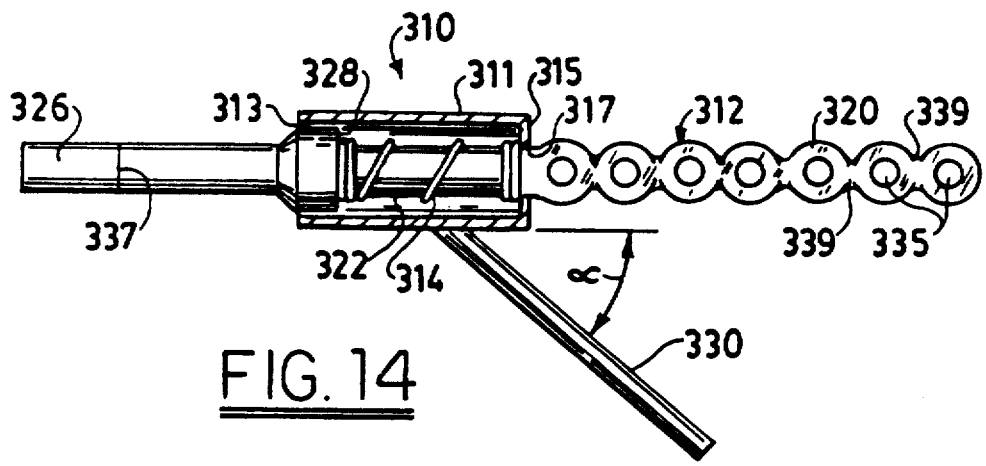
FIG. 14 is a front elevational view, partially broken away, of a modified tensioning device made in accordance with the present invention.

Referring to FIG. 14, there is illustrated another orthodontic tensioning device 310 made in accordance with the present invention. The device 310 comprises a generally cylindrical mounting tube 311, an elongated elastic member 312 and spring 314. Mounting tube 311 has an opening end 313 for allowing assembly of elastic member 312 and spring 314 into tube 311 at one end, and an end wall 315 at the other end. The end wall 315 has a narrow opening 317 for allowing elongated elastic member 312 to pass through. The spring 312 is disposed within tube 311 and has one end which presses against the inside surface of end wall 315. The opening 317 is of sufficient size to allow passage of elastic member 312 therethrough, but small enough so as to prevent spring 314 from passing through. The elastic member 312 is designed to pass through the central opening of spring 314 and narrow opening 317 and is preferably a single integrally molded piece made of an elastic material. Member 312 comprises a retention section 320 designed to be secured to an orthodontic fixture, for example a hook on an archwire, a central portion 322 for placement within tube 311 and spring 314, a terminal end 324 and a detachable tail section 326. Terminal end 324 has an outer configuration which substantially mates with the inside surface of tube 311 and has a shoulder 328 adjacent central portion 312 for placement against the outer end 329 of spring 314 such that when an axial force is placed on retention section 320, spring 314 will be placed in compression. Secured to tube 311 is a mounting pin 330. The pin 330 is designed to be placed within an orthodontic buccal tube and the outer exposed end bent around so as to secure the tube 311 thereto. The mounting pin is orientated at an angle $\alpha$ with respect to the longitudinal axis X-X of tube 311, preferably in the range of about 30° to 50°. In the particular embodiment illustrated, angle $\alpha$ is about 33°. The device is simply assembled by passing retention section 320 through spring 314, tube 311, and opening 317. Once assembled, the detachable tail 326 may be cut off at point 337 adjacent terminal end 315. Tube 311 protects spring 314 from the oral environment and minimizes debris from being caught therein. Retention section 320 in the embodiment illustrated, is provided with a plurality of openings 335 and has a configuration similar to a plurality of attached O-rings having connections 339. The retention section 320 may be cut to the device length using any appropriate opening 335 for mounting to an orthodontic fixture. It is to be understood that retention section 312 may take other desired shapes and configurations.

Applicants have found that orthodontic tensioning devices, made in accordance with the present invention, provide improved force retention after initial elongation of the device. The embodiments, as illustrated in FIGS. 1-8, were compared with a prior art elastic tensioning device of the type illustrated in FIG. 16. The prior art device simply comprises an elastomeric device formed in the shape of a dumbbell made of a typical prior art elastomer. The prior art device tested was made of a thermoplastic polyurethane elastomer having Shore A hardness in the range of 80 to 90. The devices were tested by first elongating the device a distance of 30 mm (1.181 inches) and the amount of initial force to stretch the device measured. After a five (5) minute time period, the force necessary to maintain the device at the 30 mm elongation is again measured. The following table sets forth the results of a test comparing the present invention with the prior art as it relates the present force retained in comparison to the initial force applied. It will be seen that the device according the present invention shows significant improvement over the prior art.

TABLE A

| | PERCENT FORCE RETAINED | |
|---|---|---|
| DEVICE | AMOUNT ELONGATION 30 mm | AMOUNT ELONGATION 20 mm |
| Prior Art Device | 45 | 49 |
| Type I Device | | |
| Configuration A | 69 | 62 |
| Configuration B | 78 | 70 |
| Configuration C | 80 | 68 |
| Configuration D | 65 | 75 |
| Type II Device | | |
| Configuration E | 94 | 100 |
| Configuration F | 85 | 100 |

Type I device refers to a device made in accordance with the embodiment illustrated in FIGS. 1-5. The device of Type I was tested using four different configurations. In configuration A, an elastic material having Shore A Hardness of 80 and a spring made out of super elastic Nitinol was used. In particular, elastic members 12 were made of a polyurethane sold by Dow Chemical Company, identified as Dow Pellethane 2363-80A. The members 12 had a cross-sectional diameter D of about 0.090 inches in the central section. The spring 14 was made of Nitinol 45-55, purchased from the Furakawa Corporation of Japan, having a length of about 0.5 inches, inside diameter 0.090, an outside diameter of 0.118 inches, and made of a wire having a cross-sectional diameter of about 0.014 inches. The spring 14 had 6 open coils with two closed coils at each end. Configuration B is similar to that of Configuration A, except that members 12 were made of an elastic material having a Shore A 70 hardness, in particular, members 12 were made of a polyurethane sold by Dow, Dow Pellethane 2363-70A. Configuration C is also similar to Configuration A, except that elastic member 12 is made with a material having a Shore A 55 Hardness. In particular, a polymer purchased from Concept Polymer Technology sold under C-Flex HR-70-55 product code. Configuration D used the same elastic material as Configuration A, except a stainless steel spring was used. The spring had a length of 0.5 inches, an inside diameter of 0.125 inches, an outside diameter of 0.155 inches, a wire diameter of 0.015 inches. The spring had six open coils pinched at their ends.

As can be seen from the foregoing Table A, the device of FIGS. 1-4 exhibit a percent retained force from 62 to 80 as compared to 45% to 49% of the prior art. Thus, a significant improvement in force retention was obtained by the present invention. The Type II device refers to a device as illustrated in FIGS. 6-8. In Configuration E the elastic members 112 are made of an elastic material having a Shore A hardness of 70 as in configuration B and spring 114 was made of shape memory alloy like that of Configuration A. The type II device showed significant retention of the initial force applied (94 to 100%). In Configuration F, a steel spring was used similar to that described with Configuration D. Here again, significant force retention was relevant.

Figure 15:
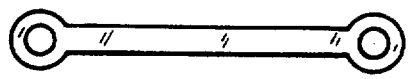
FIG. 15 is a perspective view of a prior art elastic device.

The type I device provides a structure which minimizes the potential permanent set that can occur with prior art elastic devices. Type I device has a greater effective elastic length than a single elastic prior art device 310 as illustrated in FIG. 15. The two members 12 provide an effective elastic length from the retention point in each retention section 20 greater than the prior art. Referring to FIG. 13, the actual length AL between the two retention points is represented by AL. Since member 12 overlaps in length in the area of spring 14, the length of elastic member 12 available for elongation is represented by the length D (see FIGS. 2 and 13). Thus, the available length of elastic material in the present invention is greater than the prior art by an amount equal to two times DL, the distance DL representing the amount of overlap of each member 12. Thus greater elongation can be obtained without going beyond the elastic limit of the individual member 12.

Figure 16:
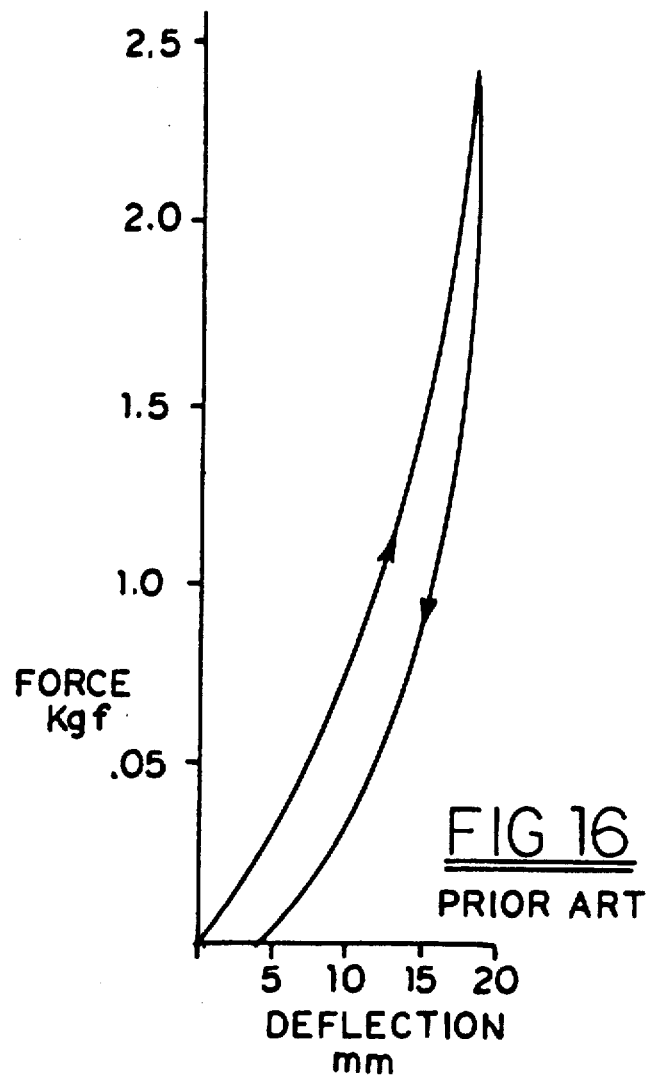
FIG. 16-22 illustrate various load deflection curves for devices made in accordance with the present invention and prior art.
Figure 17:
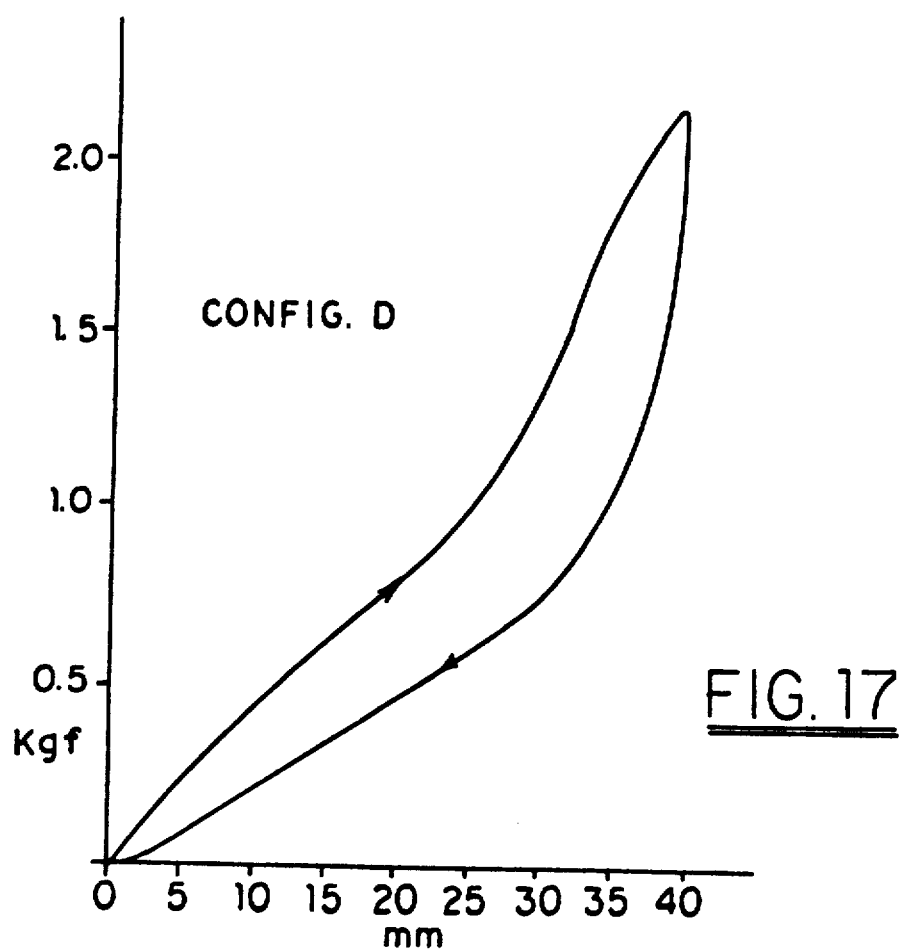
Figure 18:
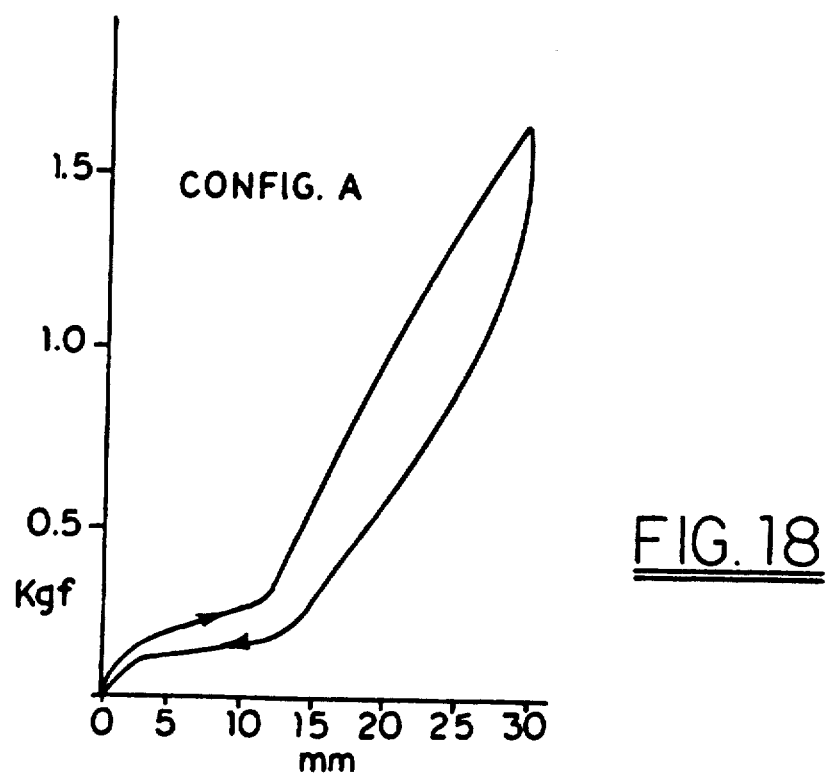
Figure 19:
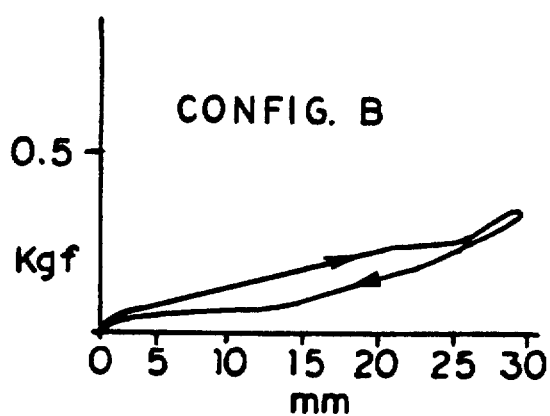
Figure 20:
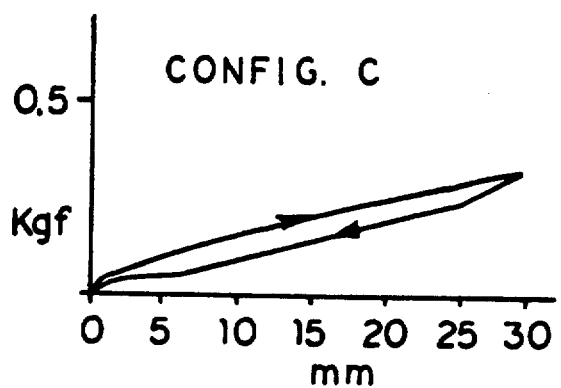
Figure 21:
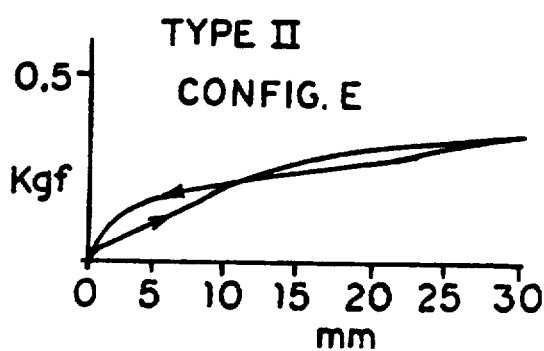
Figure 22:
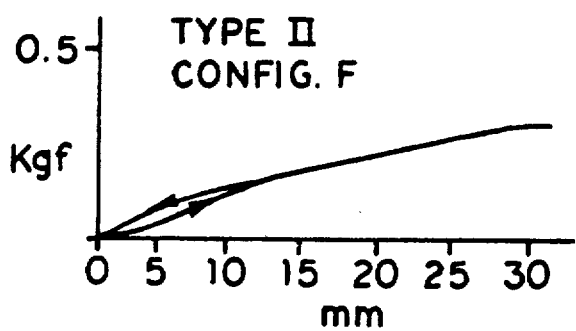

In addition to providing improved force retention and minimizing the potential of causing permanent set, orthodontic tensioning devices according to the present invention provide substantially constant force during elongation. FIG. 16 illustrates the load deflection curve for the prior art device of Table A for the 30 mm deflection. As can be seen, the force required to elongate the device rises rapidly to a relatively high force level. FIGS. 17, 18, 19 and 20 illustrate the load deflection causes for Configurations A, B, C, D, respectively for the type 1 device of Table A for 30 mm deflection. As can be seen the maximum force is substantially reduced and a relative constant force can be obtained for wide variations in deflection. Also by varying the properties of the elastic material relative constant forces can be obtained over substantially the entire elongation as illustrated in FIGS. 19 and 20. FIG. 21 illustrates the load deflection curve for the Configuration E type II device of Table A for 30 mm deflection. In this embodiment the load applied reached a substantially constant level quickly. FIG. 22 illustrates the load deflection curve for Configuration F, Type II device.

As can be seen the force applied by tensioning devices according to the present invention can be maintained in ranges of about 2 to 10 ounces, or preferably within the range of 4 to 8 ounces. The present invention allows the selection of appropriate elastic material to obtain predetermined tensioning forces as desired.

It is to be understood that various changes and modifications may be made without departing from the scope of the present invention which is defined by the following claims. For example, but not by way of limitation, the coil spring may be of any material capable of providing the desired force, such as plastic or other composite material.

What is claimed is:

1. An orthodontic tensioning device for use in straightening teeth and/or jaws comprising:
    at least one stretchable elastic tensioning member for applying a tensioning force in a single axial direction;
    a second stretchable tensioning member made of a non-elastic material for providing a tensioning force in a single axial direction, said second tensioning member cooperating with said at least one electric tensioning member so as to provide a predetermined tensioning force in the same axial direction, said second tensioning member being a separate element from said at least one electric tensioning member wherein said at least one elastic tensioning member comprises a pair of elastomeric tensioning members, said second tensioning member being secured in series between said pair of elastomeric tensioning members.

2. An orthodontic tensioning device according to claim 1 wherein said second tensioning member comprises a coil spring.

3. An orthodontic tensioning device according to claim 1 wherein said coil spring is made of a shape member alloy.

4. An orthodontic tensioning device designed for placement in the mouth of a patient for use in straightening teeth and/or jaws comprising:
   (a) a pair of elongated members placed adjacent each other in a sliding relationship for movement in opposite directions, each of said members having an outer terminal end, and an inner retention section having means for anchoring each of said members to an orthodontic fixture; and
   (b) a coil spring surrounding said pair of elongated members so as to hold said first and second members in longitudinal alignment so that they can slide along their longitudinal axis, said first and second members cooperating with said coil spring so as to place said coil spring in compression and provide a predetermined tensioning force.

5. An orthodontic tensioning device according to claim 4 wherein at least one of said elongated members is made of an elastic material.

6. An orthodontic tensioning device according to claim 5 wherein said at least one elongated member made of an elastic material is further provided with a detachable inner tail section formed at the end of said retention section, said detachable inner tail section having a cross-sectional configuration designed to allow placement through said coil spring at the same time as an other inner tail of said other member of said pair is placed within said coil spring so as to allow assembly of said first and second members within said coil spring.

7. An orthodontic tensioning device for use in straightening teeth and/or jaws comprising:
   at least one stretchable elastic tensioning member for applying a tensioning force in a single axial direction;
   a second stretchable tensioning member made of a non-elastic material for providing a tensioning force in a single axial direction, said second tensioning member cooperating with said at least one elastic tensioning member so as to provide a predetermined tensioning force in the same axial direction, said second tensioning member being a separate element from said at least one elastic tensioning member;
   a hollow tube, said hollow tube having a closed end and a oppositely disposed open end, said closed end having an opening, said second tensioning member being a coil spring, said coil spring being placed in said hollow tube such that it can not pass out said opening in said closed end, said at least one elastic tensioning member comprising an elongated elastic member having a terminal end placed against one end of said coil spring so as to compress said coil spring in said tube, said elongated elastic member extending out said open end of said tube, and having an anchor pin secured to said tube for securing said tube to an orthodontic appliance.

8. An orthodontic tensioning device according to claim 7 wherein said anchor pin is oriented at an angle from about 30° to 50° with respect to the longitudinal axis of said tube.

9. An orthodontic tensioning device according to claim 8 wherein said anchor pin is oriented at an angle of about 33° with respect to the longitudinal axis of said tube.

10. A method of assembling an orthodontic tensioning device designed for placement in the mouth of a patient for use in straightening teeth and/or jaws comprising:
   (a) providing a pair of elongated members, each of said elongated members having an outer terminal end, a central body section, a retention section, and an inner detachable tail section;
   (b) providing a coil spring member having an inner opening of sufficient size to allow placement of said pair of elongated members therethrough; and
   (c) passing the inner detachable tail section of each of said pair of elongated members through opposite ends of said spring so as to cause the terminal end of said elongated members to rest against the closest end of said spring.

* * * * *

UNITED STATES PATENT AND TRADEMARK OFFICE
CERTIFICATE OF CORRECTION

PATENT NO. : 5,074,784

DATED : December 24, 1991

INVENTOR(S) : Sterrett et al.

It is certified that error appears in the above-identified patent and that said Letters Patent is hereby corrected as shown below:

Col. 2, line 5, after "member" insert --.--

Col. 3, line 17, after "20" insert --.--

Col. 7, line 47, "FIGS. 1-4" should be --FIGS. 1-5--

Signed and Sealed this

Seventh Day of September, 1993

Attest:

BRUCE LEHMAN

Attesting Officer     Commissioner of Patents and Trademarks